US012465759B2

(12) United States Patent
Kriman et al.

(10) Patent No.: US 12,465,759 B2
(45) Date of Patent: Nov. 11, 2025

(54) ELECTROSTATIC THERAPEUTIC DEVICE

(71) Applicants: Boris Kriman, Grand Bahama (BS); Vladimir Kriman, Grand Bahama (BS)

(72) Inventors: Boris Kriman, Grand Bahama (BS); Vladimir Kriman, Grand Bahama (BS)

( * ) Notice: Subject to any disclaimer, the term of this patent is extended or adjusted under 35 U.S.C. 154(b) by 0 days.

(21) Appl. No.: 18/688,595

(22) PCT Filed: Mar. 29, 2023

(86) PCT No.: PCT/IB2023/053145
§ 371 (c)(1),
(2) Date: Mar. 1, 2024

(87) PCT Pub. No.: WO2024/189415
PCT Pub. Date: Sep. 19, 2024

(65) Prior Publication Data

US 2025/0256094 A1 Aug. 14, 2025

Related U.S. Application Data

(60) Provisional application No. 63/490,095, filed on Mar. 14, 2023.

(51) Int. Cl.
*A61N 1/10* (2006.01)
*A61N 1/04* (2006.01)
*A61N 1/40* (2006.01)

(52) U.S. Cl.
CPC ............ *A61N 1/10* (2013.01); *A61N 1/0408* (2013.01); *A61N 1/40* (2013.01)

(58) Field of Classification Search
CPC .......... A61N 1/10; A61N 1/0408; A61N 1/40
See application file for complete search history.

(56) References Cited

U.S. PATENT DOCUMENTS

| | | | |
|---|---|---|---|
| 3,750,672 | A | 8/1973 | Von Berckheim |
| 3,885,573 | A | 5/1975 | Hara |
| 4,094,322 | A | 6/1978 | Hara |
| 4,292,980 | A | 10/1981 | Suzuki |
| 4,802,470 | A | 2/1989 | Hara et al. |

(Continued)

FOREIGN PATENT DOCUMENTS

| | | | |
|---|---|---|---|
| CH | 0113618 | A | 9/2018 |
| CN | 101389375 | B | 3/2012 |

(Continued)

OTHER PUBLICATIONS

U.S. Appl. No. 16/506,633, filed Feb. 21, 2023, N Kaynan et al.

(Continued)

*Primary Examiner* — Mark W. Bockelman

(57) ABSTRACT

An electrostatic therapeutic device and a method of therapeutic treatment are disclosed. The electrotherapy device includes a charge generation module, at least one therapeutic electrode and an electrical drive. The charge generation module contains at least one closed loop dielectric belt, put on at least one pair of dielectric pulleys and a set of charging and discharging electrodes. Rotation of the dielectric pulleys generates an electric charge of a predetermined polarity on the at least one therapeutic electrode. The reversed rotation reverses the polarity. The device is intended for patient's body exposure to an alternating electric field.

10 Claims, 18 Drawing Sheets

(56) References Cited

U.S. PATENT DOCUMENTS

| | | | | |
|---|---|---|---|---|
| 4,846,178 | A | 7/1989 | Zhang | |
| 4,976,263 | A | 12/1990 | Seidl et al. | |
| 5,031,617 | A | 7/1991 | Klettner | |
| 5,899,922 | A | 5/1999 | Loos | |
| 6,167,304 | A | 12/2000 | Loos | |
| 7,890,183 | B2 | 2/2011 | Palti et al. | |
| 8,287,475 | B2 | 10/2012 | Smithers et al. | |
| 9,504,823 | B2 | 11/2016 | Oh | |
| 10,589,091 | B2 | 3/2020 | Hirsovitz et al. | |
| 2003/0083185 | A1 | 5/2003 | Trennepohl | |
| 2010/0224126 | A1 | 9/2010 | Kriman | |
| 2018/0055720 | A1* | 3/2018 | Sitkovetskiy | A61N 1/10 |

FOREIGN PATENT DOCUMENTS

| | | | |
|---|---|---|---|
| CN | 201410659825.4 | A | 6/2016 |
| DE | 1181826 | B | 11/1964 |
| DE | 3139677 | A1 | 9/1983 |
| GB | 4824866 | A | 6/1969 |
| GB | 2261127 | A | 8/1995 |
| GB | 2274593 | A | 8/1996 |
| JP | 2006000567 | A | 8/2008 |
| RU | 32418 | A1 | 9/1993 |
| RU | 2215559 | | 11/2003 |
| RU | 2355437 | C2 | 5/2009 |

OTHER PUBLICATIONS

U.S. Appl. No. 10/417,142, filed Dec. 18, 2003, A. Hara.

U.S. Appl. No. 11/910,550, filed Jun. 4, 2009, Takuji Hara.

U.S. Appl. No. 11/014,461, filed Aug. 25, 2005, A. Hara.

U.S. Appl. No. 11/596,315, filed Nov. 8, 2007, A. Hara et al.

U.S. Appl. No. 10/581,110, filed Dec. 13, 2007, H. Suzuki et al.

* cited by examiner

2100

ELECTROSTATIC THERAPEUTIC DEVICE

CROSS-REFERENCE TO RELATED APPLICATION

This application is the national stage application of PCT application no. PCT/IB2023/053145 filed on Mar. 29, 2023, where PCT claims priority to, and the benefit of U.S. Provisional Patent Application No. 63/490,095 entitled "Electrostatic Therapeutic Device" and filed on Mar. 14, 2023, both of which are herein incorporated herein by reference in its entirety.

BACKGROUND

Technical Field

The embodiments herein generally relate to electric therapeutic devices, and more particularly, to an electrostatic therapeutic device.

Description of the Related Art

The tissues in the human body are electrically conductive. Under the action of an electric field, electrostatic polarization occurs in the tissues. The movement of electrically charged electrodes and a change in the polarity of the voltage between them induce alternating microcurrents in the tissues of the human body. These alternating microcurrents cause various physiological effects: pain relief, relaxation, lowering blood sugar levels, and the like.

Existing electrostatic therapeutic devices contain either a high voltage transformer or a voltage multiplier with a transformer, which make inducing of the electric field unsafe and a need for protecting the existing electrostatic therapeutic devices against electrical breakdown makes the devices expensive.

Accordingly, there remains a need to provide a safe, lightweight, efficient, and easy to manufacture electrotherapy device for applying a high voltage alternating electric field to the body of a patient or human.

SUMMARY

This Summary is provided to introduce a selection of concepts in a simplified form that are further described below in the Detailed Description. This Summary is not intended to identify key or essential features of the claimed subject matter, nor is it intended to be used as an aid in determining the scope of the claimed subject matter.

In one aspect an electrostatic therapeutic device is disclosed. An electrostatic therapeutic device includes a charge generating unit, the at least one therapeutic electrode, an electric drive unit, and an electric circuit. The charge generating unit includes: a. two parallel rotating shafts; b. at least one pair of pulleys mounted on the two parallel rotating shafts, where a first pulley from every pair of pulleys is mounted on a first shaft, and a second pulley from every pair of pulleys is mounted on a second shaft, where the pair of pulleys are made of a dielectric material, and configured to be triboelectrically charged with an electric charge of same polarity based on a triboelectric interaction with a closed loop belt upon rotation of the two parallel rotating shafts; c. at least one closed loop belt stretched over the at least one pair of pulleys to transfer an electric charge between a pair of terminals of a charge generating unit, where the closed loop belt is made of a dielectric material; d. a pair of terminals of a charge generating unit, for coupling the charge generating unit with at least one therapeutic electrode; e. a pair of charging electrodes for charging the at least one closed loop belt, wherein a first charging electrode from among the pair of charging electrodes is positioned over the at least one belt against the pulleys mounted on the first shaft and connected to the first terminal of the charge generating unit, and where a second charging electrode from among the pair of charging electrodes is positioned over the belt against the pulleys mounted on the second shafts and connected to the second terminal of the charge generating unit, and f. a pair of discharging electrodes for discharging the at least one closed loop belt, wherein a first discharging electrode of the pair of discharging electrodes is positioned over the belt at a distance from the first shaft and electrically connected to the first terminal of the charge generating unit, and where a second discharging electrode from among the pair of discharging electrodes is positioned over the belt at a distance from the second shaft and electrically connected to the second terminal of the charge generating unit.

The at least one therapeutic electrode is coupled with the at least one terminal of the two terminals of the charge generating unit to enable applying an electrical charge to the patient's body. Every therapeutic electrode is coupled with only one of the two terminals of the charge generating unit. The electric drive unit rotates the pair of the shafts and the at least one closed loop belt in a clockwise direction and an anticlockwise direction. The electric circuit switches the rotation of an electric drive unit with a predetermined frequency. The electric charge generated due to the triboelectric interaction between the at least one closed loop belt and the at least one pair of dielectric pulleys is transferred to the at least one therapeutic electrode, where the at least one therapeutic electrode accumulates the electric charge of a predetermined polarity when the at least one pair of pulleys and the at least one closed loop belt rotate in the clockwise direction, and where the at least one therapeutic electrode accumulates the electric charge of a reverse polarity when the at least one pair of pulleys and the at least one closed loop belt rotate in the anti-clockwise direction, and where the body of the patient is therapeutically treated by microcurrents caused by an alternating electric charge on the at least one therapeutic electrode.

In an embodiment, the electrostatic therapeutic device includes a shell made of a conductive or a semi conductive material and coupled with a terminal of the charge generating unit. One charging electrode and one discharging electrode connected to the same terminal of the charge generating unit are located inside the shell to improve electric charge transfer between the at least one closed loop belt and the charging and discharging electrodes.

In an embodiment, one of the terminals of the charge generating unit is grounded.

In an embodiment, a first therapeutic electrode is shaped as a handle for holding the therapeutic device by a patient or therapist. When electric drive unit rotates, electric charge of one polarity is released into body of the patient or therapist via the handle, and electric charge of the opposite polarity is accumulated at a second therapeutic electrode placed at a distance over the body of a patient.

In an embodiment, the electrostatic therapeutic device includes an attachment to hold the at least one therapeutic electrode at a predetermined distance from the body of a patient.

In another aspect a method of therapeutic treatment is disclosed. The method includes rotating at least one closed loop belt stretched over at least one pair of pulleys of an electrostatic therapeutic device. Upon rotation of the at least one pair of pulleys, the at least one closed loop belt moves around the at least one pair of pulleys and an electric charge of a predetermined polarity is triboelectrically generated at a surface of the at least one closed loop belt and transferred with at least one closed loop belt between two terminals of an electric charge generating unit of an electrostatic therapeutic device. The method includes transferring the generated electric charge from at least one terminal of an electric charge generating unit to at least one therapeutic electrode. The method includes reversing rotation of the at least one closed loop belt to reverse polarity of an electric charge on the terminals of the charge generating unit. The method includes applying an alternating electric charge of at least one therapeutic electrode to the body of a patient to induce microcurrents therein.

In an embodiment, a patient is placed on a dielectric platform and at least one therapeutic electrode is electrically connected to the body of the patient for transferring an electrical charge thereto.

In an embodiment, the patient is placed on a platform made of a dielectric material. The patient's body is placed in an electric field between at least two therapeutic electrodes of different polarities so that the patient's body is not in contact with them.

In an embodiment, the electrostatic therapeutic device is designed as a portable wand. A first therapeutic electrode is designed as a handle of the portable wand, and a patient or a therapist holds the handle of the portable wand to place a second therapeutic electrode over different areas of a body of the patient.

In an embodiment, at least one therapeutic electrode is positioned at a distance from the body of the patient.

The instant application solves all of the foregoing problems by providing a safe, lightweight, efficient, and easy to manufacture electrotherapy device for applying a high voltage alternating electric field to the body of a patient. The present technology has no risk of malfunctions and failures caused by electrical breakdowns in the electrostatic therapeutic device, which can occur in a transformer or in high voltage semiconductor elements. Further, the electrostatic therapeutic device of the present technology does not have conductive points that could be dangerous to a user. Additionally, the electrostatic therapeutic device of the present technology does not require special circuits to protect a user from electric shock. Moreover, the electrostatic therapeutic device of the present technology acts on the patient with an electric field, inducing micro-currents in the patient's body as a whole or its specific target area.

BRIEF DESCRIPTION OF THE DRAWINGS

The embodiments herein will be better understood from the following detailed description with reference to the drawings, in which.

DETAILED DESCRIPTION OF PREFERRED EMBODIMENTS

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Figure 1:
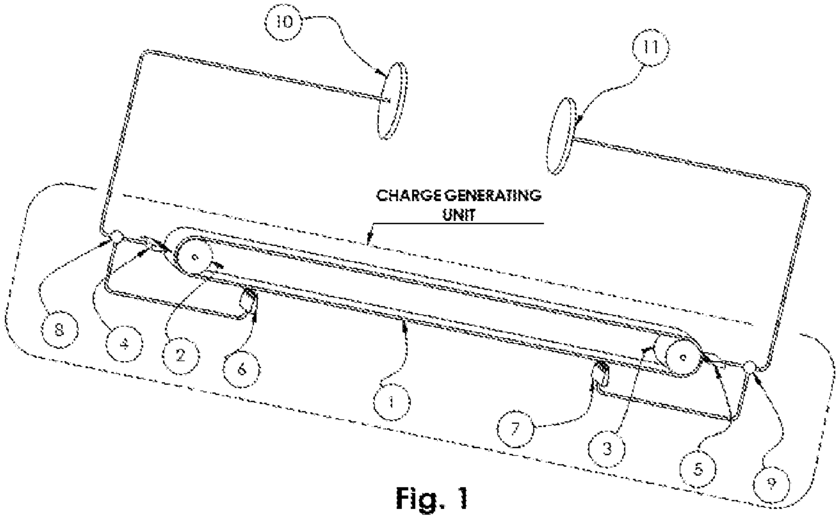
FIG. 1 depicts a perspective view of an electrostatic therapeutic device of the present technology, in accordance with an embodiment.

Various embodiments disclosed herein provide an electrotherapeutic device that includes a charge generating unit including two parallel rotating shafts, at least one pair of pulleys mounted on the two parallel rotating shafts, at least one closed loop belt stretched over the at least one pair of pulleys to transfer an electric charge between a pair of terminals of a charge generating unit. FIG. 1 depicts a perspective view of an electrotherapeutic device of the present technology, in accordance with an embodiment. An electrostatic therapeutic device comprises a charge generating unit circled by a dot-dashed rectangle and two therapeutic electrodes 10 and 11. The charge generating unit includes one closed loop belt 1, two parallel rotating shafts (not shown), one pair of the pulleys 2 and 3, a pair of the charging electrodes 4 and 5, a pair of the discharging electrodes 6 and 7 and a pair of the terminals 8 and 9 for connecting with the therapeutic electrodes. The electrodes 4,5,6,7 have sharp tips, and these sharp tips are turned towards the belt surface. The first charging electrode 4 is positioned over the closed loop belt 1 against the pulley 2. The second charging electrode 5 is positioned over the closed loop belt 1 against the pulley 3. The first discharging electrode 6 is positioned over the closed loop belt 1 at a distance from the first pulley 2. The second discharging electrode 7 is positioned over the closed loop belt 1 at a distance from the second pulley 3. Both discharging electrodes are positioned along one side of the closed loop belt 1. The first charging electrode 4 and the first discharging electrode 6 are electrically connected to the first output terminal 8 of the charge generating unit. The second charging electrode 5 and the second discharging electrode 7 are electrically connected to the second output terminal 9 of the charge generating unit. Pulleys 2 and 3 are made of a well electrified material, for example PTFE. The closed loop belt is made of an elastic dielectric material, for example a synthetic rubber.

Figure 2:
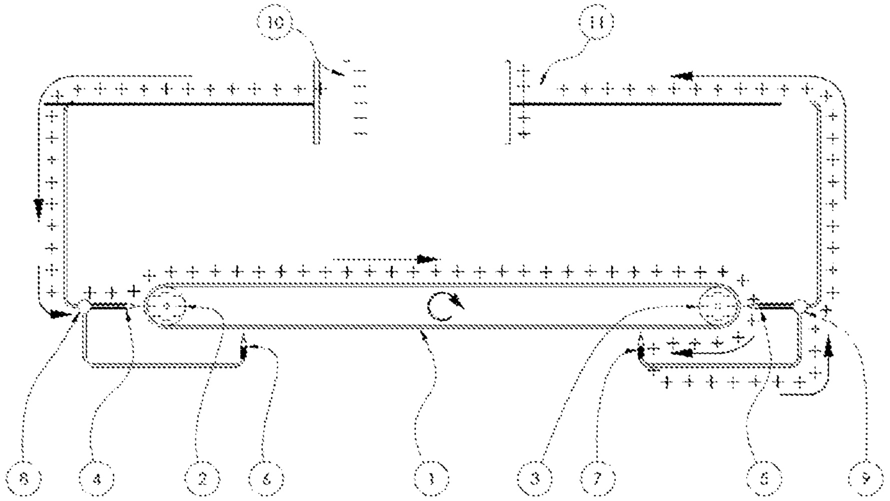
FIG. 2 illustrates an operation of the electrostatic therapeutic device of FIG. 1, during a clockwise rotation of the charge-carrying belt, in accordance with an embodiment.
Figure 3:
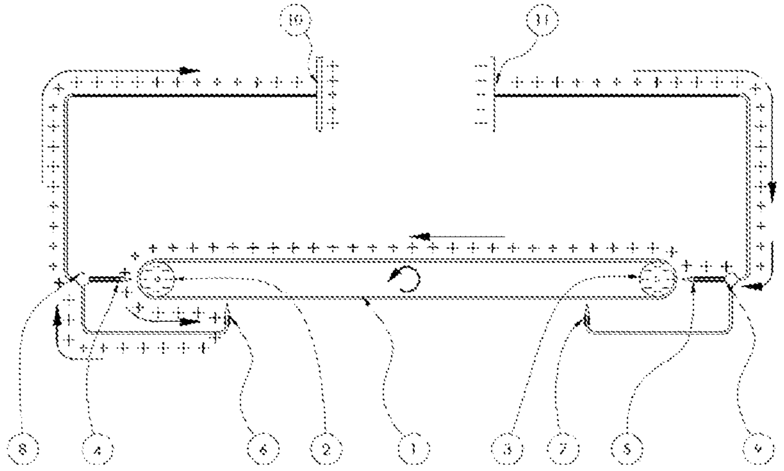
FIG. 3 illustrates an operation of the electrostatic therapeutic device of FIG. 1, during an anticlockwise rotation of the charge-carrying belt, in accordance with an embodiment.

FIGS. 2 and 3 illustrate operation of the electrostatic therapeutic device of FIG. 1. More particularly, FIG. 2 depicts a diagram of movement of electric charges during a clockwise rotation of the charge-carrying belt. When the belt 1 rotates, the pair of pulleys 2 and 3 get charged negatively as a result of their triboelectric interaction with the belt material. An electric field arises between the negatively charge pulley 2 and the charging electrode 4. Due to enhancement of electric field near the sharp end of the charging electrode 4, the air at the electrode 4 is ionized and positive ions are formed. The positive ions are attracted by the negatively charged pulley 2. Since the belt 1 is positioned between the pulley 2 and the charging electrode 4, the positive ions settle on the outer surface of the moving belt 1 and are transferred by the belt toward the pulley 3. The pulley 3 is also negatively charged as a result of its triboelectric interaction with the belt material. Under the influence of the electric field of the negative electric charges on the surface of the pulley 3 the positive charges on the outer surface of the belt 1 are even more attracted to the belt. The positive charges move together with the belt 1, pass by the pulley 3 and turn out to be near the discharging electrode 7. The discharging electrode 7 is positioned at such a distance from the pulley 3 that the electric field generated by the pulley 3 near the tip of the discharging electrode 7 is so weak that the pully 3 does not affect the charges on the belt 1. As a result, an electric field arises between the positive charges on the belt 1 and the discharging electrode 7, causing ionization of the air near the tip of the discharging electrode 7. Thus, passing near the tip of the discharging electrode 7, the positively charged part of the belt 1 gets discharged. The part of the belt 1 that gets discharged by the discharging electrode 7 returns again to the pulley 2. Near the tip of the charging electrode 4, the belt 1 gets charged positively again, and the process recurs as the belt 1 rotates. Thus, when the belt 1 moves clockwise, the positive charges deposited on the belt surface near the pulley 2 move together with belt 1 and pass from the terminal 8 to the terminal 9. As a result, the therapeutic electrode 10 coupled with the terminal 8 gets charged negatively, and the therapeutic electrode 11 coupled with the terminal 9 gets charged positively.

FIG. 3 depicts a diagram of movement of electric charges during a counterclockwise rotation of the charge-carrying belt. When the belt 1 rotates counterclockwise, the pair of pulleys 2 and 3 get charged negatively as a result of their triboelectric interaction with the belt material. An electric field arises between the negatively charge pulley 3 and the charging electrode 5. Due to enhancement of electric field near the sharp end of the charging electrode 5, the air at the electrode 5 is ionized and positive ions are formed. The positive ions are attracted by the negatively charged pulley 3. Since the belt 1 is positioned between the pulley 3 and the charging electrode 5, the positive ions settle on the outer surface of the moving belt 1 and are transferred by the belt toward the pulley 2. The pulley 2 is also negatively charged as a result of its triboelectric interaction with the belt material. Under the influence of the electric field of the negative electric charges on the surface of the pulley 2 the positive charges on the outer surface of the belt 1 are even more attracted to the belt. The positive charges move together with the belt 1, pass by the pulley 2 and turn out to be near the discharging electrode 6. The discharging electrode 6 is positioned at such a distance from the pulley 2 that the electric field generated by the pulley 2 near the tip of the discharging electrode 6 is so weak that the pulley 2 does not affect the charges on the belt 1. As a result, an electric field arises between the positive charges on the belt 1 and the discharging electrode 6, causing ionization of the air near the tip of the discharging electrode 6. Thus, passing along the tip of the discharging electrode 6, the positively charged part of the belt 1 gets discharged. The part of the belt 1 that gets discharged by the discharging electrode 6 returns again to the pulley 3. Near the tip of the charging electrode 5, the belt 1 gets charged positively again, and the process recurs as the belt 1 rotates. Thus, when the belt 1 moves anticlockwise, the positive charges deposited on the belt surface near the pulley 3 move together with the belt 1 and pass from the terminal 9 to the terminal 8. As a result, the therapeutic electrode 10 coupled with the terminal 8 gets charged positively, and the therapeutic electrode 11 coupled with the terminal 9 gets charged negatively. Thus, due to the alternating rotation of the belt 1 clockwise and counterclockwise, an alternating electric field arises between the therapeutic electrodes 10 and 11, which is used for therapeutic purposes.

Figure 4:
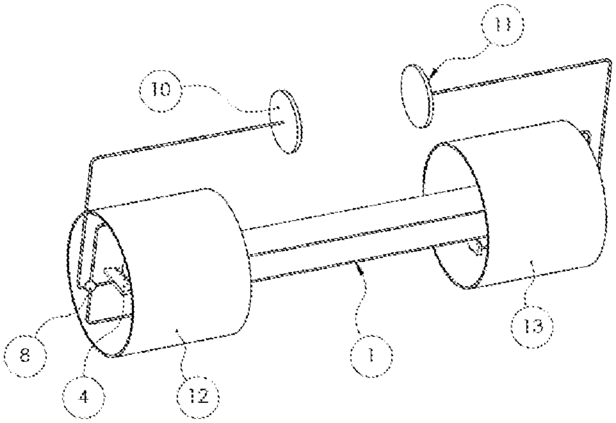
FIG. 4 depicts a perspective view of the electrostatic therapeutic device with a pair of conductive shells, in accordance with an embodiment.
Figure 5:
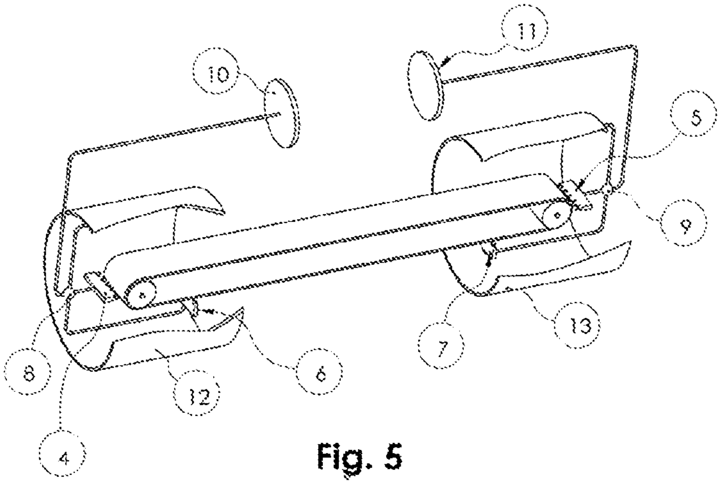
FIG. 5 depicts a cutaway view of the electrostatic therapeutic device of FIG. 4, in accordance with an embodiment.

FIGS. 4 and 5 depict perspective views of the electrostatic therapeutic device with hollow conductive shells. The conductive shells improve the process of charging and discharging of the closed loop belt 1. The conductive shells make the process more stable and less dependent on the electrical charges on the therapeutic electrodes 10 and 11, which can vary during a therapeutic treatment. The pulley 2, the charging electrode 4 and the discharging electrode 6 are positioned inside a hollow conductive shell 12. The terminal 8 is connected to the conductive shell 12. The pulley 3, the charging electrode 5 and the discharging electrode 7 are positioned inside a hollow conductive shell 13. The terminal 9 is connected to the conductive shell 13. The hollow conductive shells 12 and 13 form Faraday cages. It is known to any person skilled in the art that electric charges outside a Faraday cage do not affect electric charges inside the cage. Thus, the electric charge accumulated on the therapeutic electrodes 10 and 11 do not affect the process of electric charge transfer between the belt 1 and the electrodes 4,5,6, and 7 if they are enclosed in the hollow conductive shells 12 and 13. In an embodiment, the hollow conductive shells 12 and 13 have a continuous surface as shown in the FIG. 4. In several other embodiments, the hollow conductive shells may have a continuous surface with holes or a mesh-like surface. In several embodiments, the material of the hollow conductive shells 12 and 13 can be conductive like metal or semi-conductive like conductive plastic.

Figure 6:
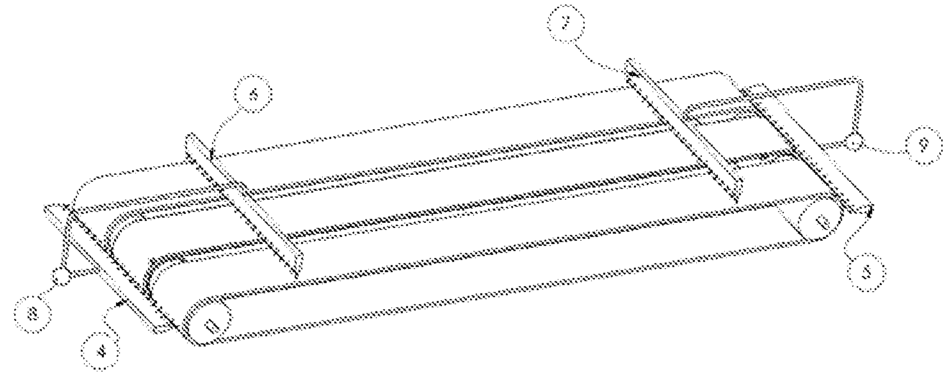
FIG. 6 depicts a perspective view of a charge-generating unit of the electrostatic therapeutic device with multiple charge-carrying belts, in accordance with an embodiment.

FIG. 6 depicts a perspective view of a charge-generating unit with multiple charge-carrying belts, in accordance with another embodiment. An amount of electrical charge on the therapeutic electrodes and the voltage between them depends on the width and speed of the charge-carrying belt. The wider the charge carrying belt and the faster it moves, the more charge it transfers, and the more charge accumulates on the therapeutic electrodes. However, increasing the width of an elastic belt moving at high speed can cause belt wrinkling and jamming. To intensify the transfer of electric charge, a single closed elastic belt could be replaced by a plurality of parallel belts rotating in the same direction, such that each belt is stretched over a separate pair of dielectric pulleys. The charge transfer rate of the plurality of closed loop belts is equal to the sum of the charge transfer rates of each belt. Each relatively narrow belt of the plurality can be rotated at high speed with no jamming. The pulleys can be mounted on two parallel axles. A charge generating unit including three charge-carrying belts is shown in FIG. 6.

Figure 7:
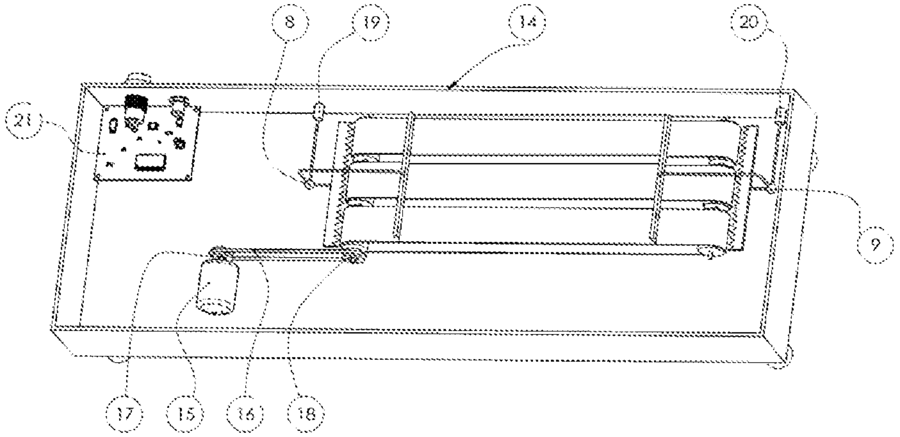
FIG. 7 depicts a perspective view of a charge-generating unit with multiple charge-carrying belts in a housing, in accordance with another embodiment.

FIG. 7 depicts a perspective view of the charge generating unit of FIG. 6 in a housing with an electric drive unit and a control module in accordance with another embodiment. The charge generating unit of FIG. 6 is positioned in a dielectric housing 14. The charge carrying belts are driven by an electric drive unit that comprise an electric motor 15, a driving belt 16 and pulleys 17, 18 to transfer the torque from the electric motor shaft to the charge generation unit. The terminals 8, 9 of the charge generating unit are coupled with sockets 19 and 20 for connecting two therapeutic electrodes. The electric motor 15 is powered through a control module 21 that switches direction of rotation of the motor shaft with a predetermined frequency.

Figure 8:
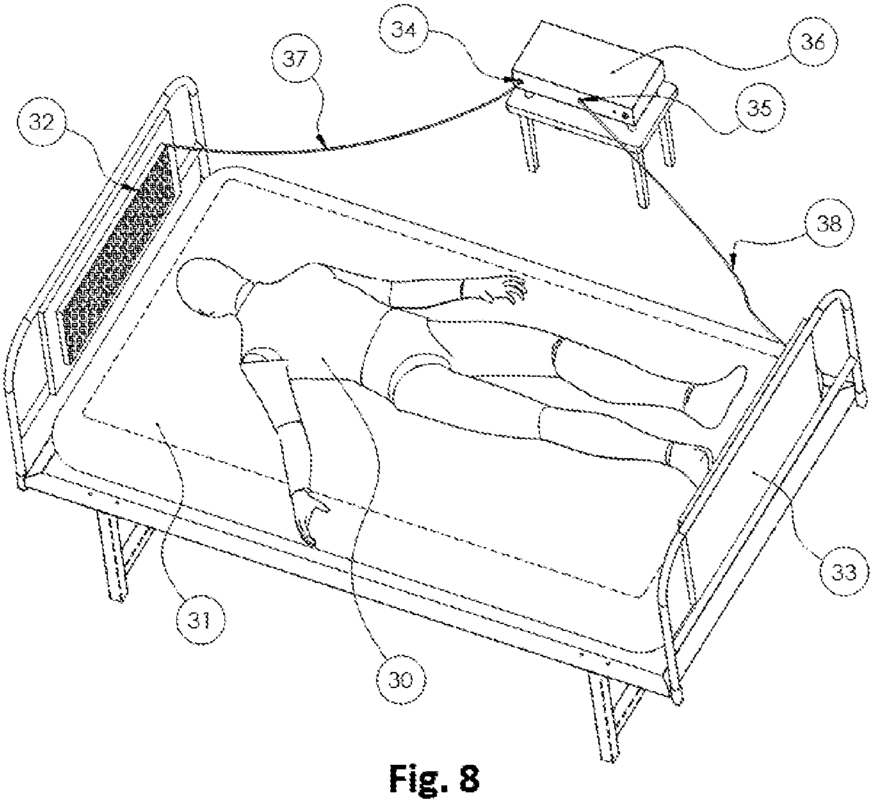
FIG. 8 depicts an exemplary use case of the electrostatic therapeutic device being used for a contactless patient treatment with an alternate electric field, in accordance with an exemplary scenario.

FIG. 8 depicts an exemplary use case of the electrostatic therapeutic device being used for a contactless patient treatment with an alternate electric field, in accordance with an exemplary scenario. For example, consider a patient 30 lies on a bed 31 made of a dielectric material. A first therapeutic electrode 32 is installed at the head of the bed and a second therapeutic electrode 33 is installed at the feet of the patient. The therapeutic electrodes 32 and 33 are connected to sockets 34 and 35 of a charge generating unit 36 with cables 37 and 38. A high voltage and a corresponding electric field are generated between the therapeutic electrodes 32 and 33. The body of the patient is subjected to non-contact electrostatic polarization. When the direction of rotation of the belt 1 in the electrotherapeutic device 36 is reversed, the polarity on the therapy electrodes is also reversed. Polarization micro-currents are induced in the body of the patient due to changes in the polarity of the surrounding electric field.

Figure 9:
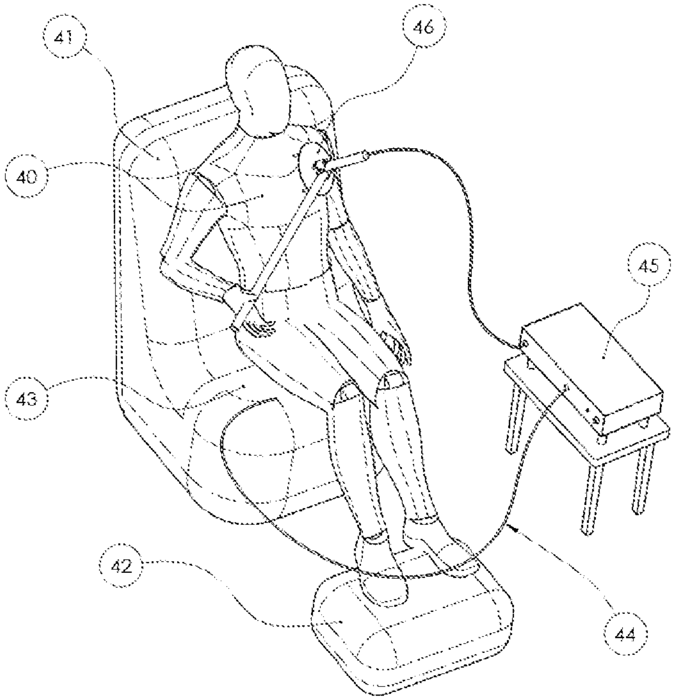
FIG. 9 depicts an exemplary use case of the electrostatic therapeutic device being used for treating a patient with one fixed therapeutic electrode connected to the patient's body and another movable therapeutic electrode positioned on a distance over a target area, in accordance with an exemplary scenario.

FIG. 9 depicts an exemplary use case of the electrostatic therapeutic device being used for treating a patient with one fixed therapeutic electrode connected to the body of the patient and another movable therapeutic electrode positioned on a distance over a target area, in accordance with an exemplary scenario. For example, consider a patient 40 sitting on a dielectric chair 41. The legs of the patient 40 rest on a dielectric support 42. A fixed therapeutic electrode 43 is located on the seat of the chair 41. The electric charge is applied to the fixed therapeutic electrode 43 through a cable 44 from a charge generating unit 45 and is transferred to the body of the patient 40. The clothing on the body of the patient 40 is not an obstacle to the passage of electric charge through it. If the clothing is made of a material with some electrical conductivity, such as cotton, then the therapeutic electrode 43 is in direct electrical contact with the body of the patient 40. If the clothing is made of a synthetic dielectric material, then the electric charge from the therapeutic electrode 43 is transferred to the body of the patient 40 as a result of electric breakdown of a small dielectric gap formed by the clothing layer.

Figure 10:
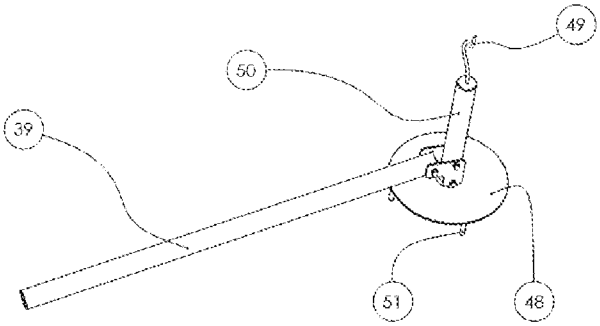
FIG. 10 depicts a first perspective view of the movable therapeutic electrode of FIG. 9, in accordance with an embodiment.
Figure 11:
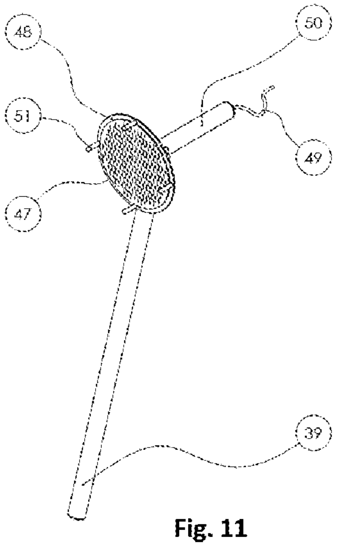
FIG. 11 depicts a second perspective view of the movable therapeutic electrode of FIG. 9, in accordance with an embodiment.

FIGS. 10 and 11 depict perspective views of the movable therapeutic electrode 46 of FIG. 9, in accordance with an embodiment. The movable therapeutic electrode 46 comprises a circular conductive plate 47 (shown in FIG. 11) attached to a plastic plate 48. A handle 39 is pivotally attached to the plastic plate 48. One end of a cable 49 is passed through a tube 50 and connected to the conductive plate 47. Another end of the cable 49 connects the conductive plate 47 to a charge generating unit 45. The tube 50 holds the cable 49 perpendicular to the surface of the patient's body so that the cable does not touch the body. Spacers 51 are attached to the plastic plate 48 to hold the conductive plate 47 at a predetermined distance from the body of the patient 40. The patient 40 moves therapeutic electrode 46 over different areas of his body. The body is charged with one polarity from the fixed therapeutic electrode 43 on the seat of the chair. The movable therapeutic electrode 46 is charged with an opposite polarity. As a result, a high potential electric field is generated between the movable therapeutic electrode 46 and the body of the patient 40. The movable therapeutic electrode 46 could be similarly held and moved over a patient body by another person.

Figure 12:
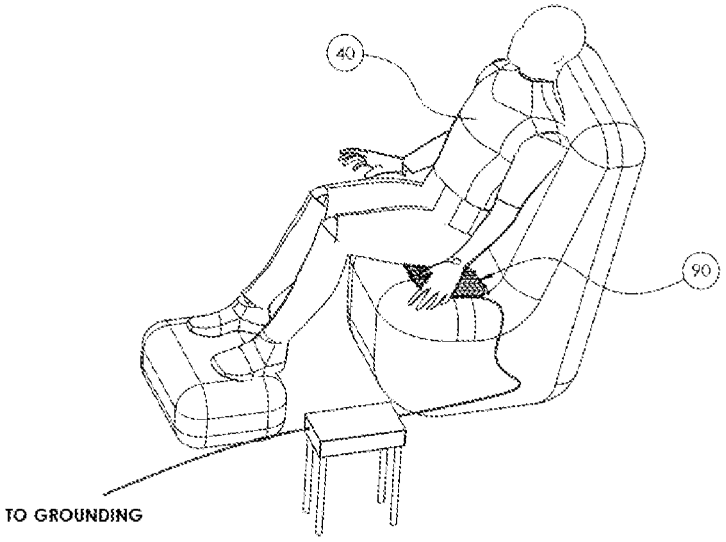
FIG. 12 depicts an exemplary use case of the electrostatic therapeutic device being used for treating a patient with one therapeutic electrode connected to the body of the patient and one grounded output of the electrostatic therapeutic device, in accordance with an exemplary scenario.

FIG. 12 depicts an exemplary use case of the electrostatic therapeutic device being used for treating a patient 40 with one therapeutic electrode connected to the body of the patient and one grounded output of the electrostatic therapeutic device, in accordance with an exemplary scenario. For example, consider the patient 40 sits on a chair. The chair is designed so that the patient 40 is isolated from the floor and other conductive and semi-conductive objects. In particular, in the FIG. 12 the patient sits on an inflatable chair with an inflatable footrest. Inflatable products are made of polymer films, which are good insulators. A conductive pad 90 is placed on the seat, and one of the outputs of the charge generating unit 91 is connected to the conductive pad 90. The second output of the charge generating unit 91 is grounded. As a result of operation of the device, electric charge of a certain polarity enters the body of the patient 40 through the conductive pad 90 on the seat. The electric charge of the opposite polarity is released to the ground. The body of the patient 40 is charging. When rotation of the electric drive unit in the device reverses, the electric charge on the body of the patient 40 changes polarity. Alternate charging of the body of the patient 40 with different polarities results in generation of alternate therapeutic microcurrents in the patient's body.

Figure 13:
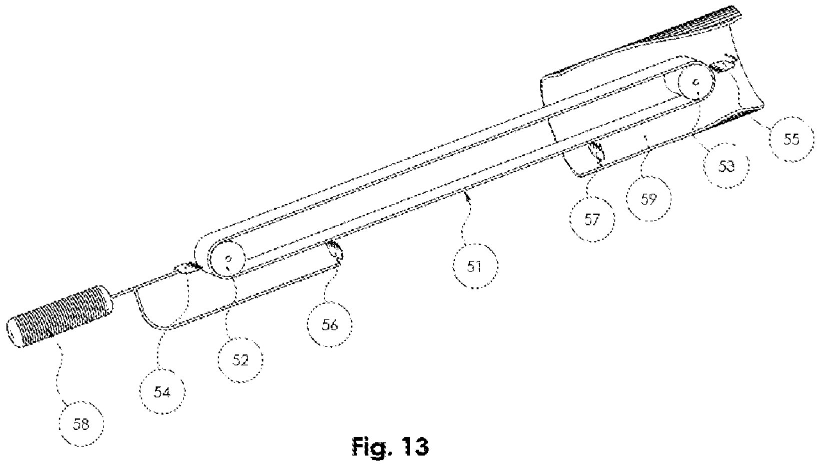
FIG. 13 is a perspective view of a diagram of an electrostatic therapeutic device, in a portable form, in accordance with yet another embodiment.

FIG. 13 is a perspective view of a diagram of an electrostatic therapeutic device in a portable form, in accordance with yet another embodiment. The electrostatic therapeutic device of FIG. 13 is made as a portable wand with a single therapeutic electrode 59. A charging electrode 55 and a discharging electrode 57 are positioned inside a hollow electrode 59. The second therapeutic electrode is a handle 58 that provides electric contact between the user's palm and electrodes 54, 56. The electrostatic therapeutic device of FIG. 13 works on the same principle as the device shown in FIG. 1-3. As an elastic belt 51 strained between dielectric pulleys 52,53 rotates, electric charge is transferred to the body of the patient through a handle 58, and an electric charge of the opposite polarity is accumulated on the hollow therapy electrode 59.

Figure 14:
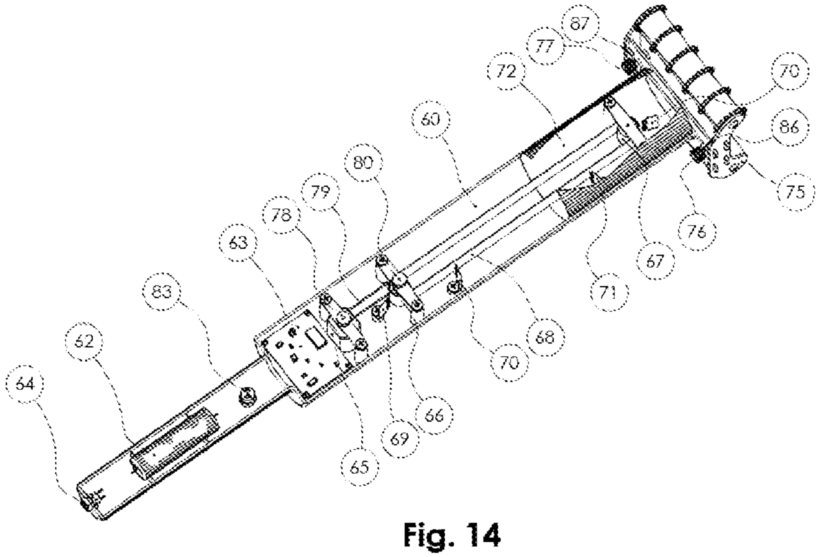
FIG. 14 is a perspective view of an electrostatic therapeutic device, in a portable form in accordance with yet another embodiment.
Figure 15:
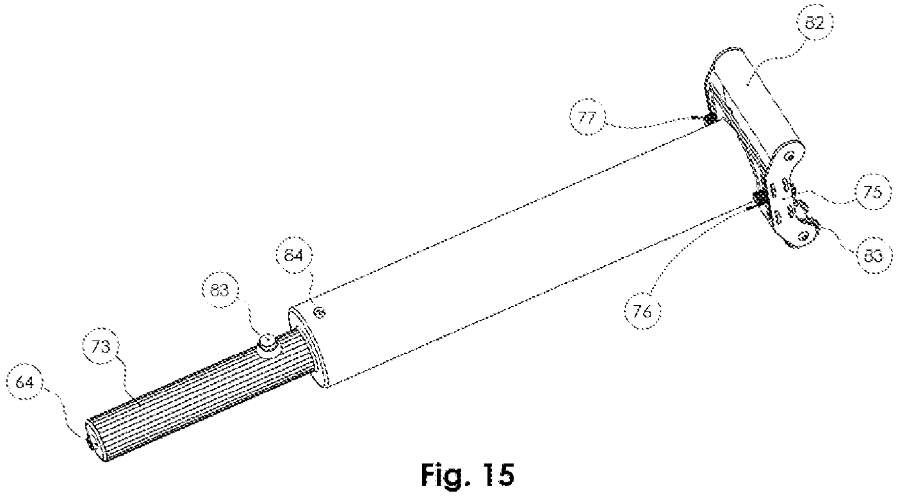
FIG. 15 is another perspective view of the electrostatic therapeutic device of FIG. 14, in accordance with an embodiment.

FIGS. 14 and 15 are perspective views of the electrostatic therapeutic device, in a portable form, in accordance with yet another embodiment. The electrostatic therapeutic device of FIG. 14,15 includes a housing 60. The following elements are located in the housing 60: a battery 62, a printed circuit board (PCB) 63, an external power connector 64, a DC motor 65, a push button 83, a Light Emitting Diode (LED) 84, a pair of pulleys 66 and 67, an elastic dielectric belt 68 strained between a pair of pulleys 66 and 67, a pair of charging electrodes 69 and 70, a pair of discharging electrodes 70 and 71, a hollow therapeutic electrode 72 and a therapeutic electrode 73 in the form of a conductive pad on the wand handle. A massage attachment 75 is attached to the housing 60 with screws 76,77. The therapeutic electrode 73 on the wand handle provides an electric contact between the pair of charging electrodes 69 and 70 and a palm of a user (patient). The PCB 63 comprises a DC motor controller and a battery charging controller. FIG. 14 shows the portable therapeutic device in the open housing 60 without a cover. FIG. 15 show the portable therapeutic device in a housing closed with the cover.

Figure 16:
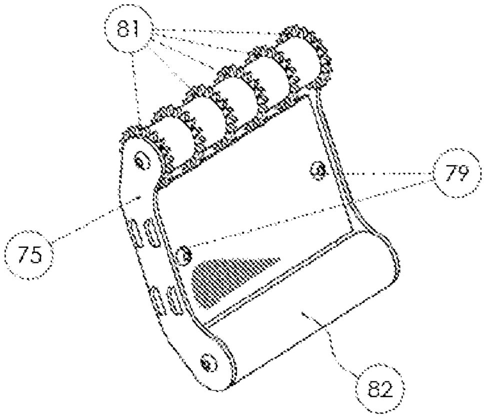
FIGS. 16,17 depict perspective views of a massaging attachment of the electrostatic therapeutic device of FIG. 14,15 in accordance with yet another embodiment.
Figure 17:
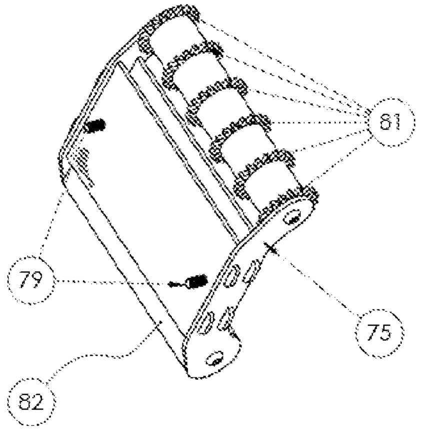

FIGS. 16-17 depict perspective views of the massaging attachment 75 of the electrostatic therapeutic device of FIG. 14, in accordance with yet another embodiment. The massaging attachment 75 is connected to housing 60 by thumb nuts 76, 77. The massaging attachment 75 of FIGS. 16-17 includes two massage elements 81 and 82. The massage element 81 includes a plurality of rotating cogwheels. The massage element 82 is a smooth plastic tube. The two screws 79 protrude from massaging attachment 75. To attach the massaging attachment 75 to housing 60, screws 84, 85 are inserted into slots 86, 87 and clamped with thumb nuts 76, 77.

Figure 18:
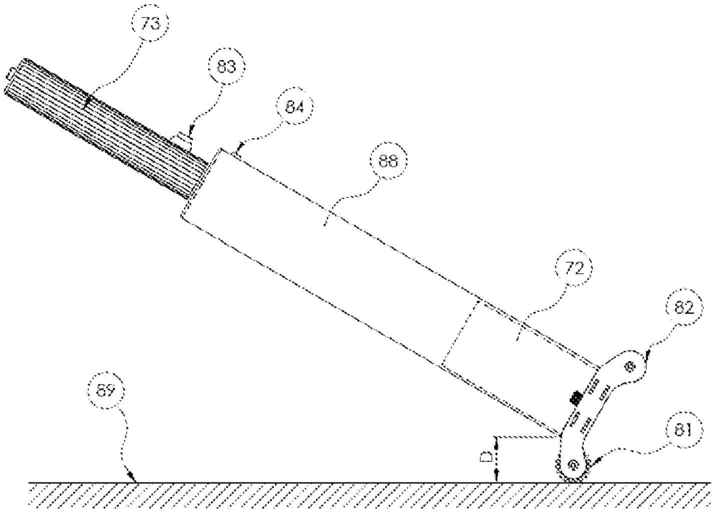
FIG. 18 depicts the massaging attachment of the electrostatic therapeutic device of FIG. 14, positioned on a massaged surface, in accordance with an exemplary scenario.

FIG. 18 depicts the portable electrotherapeutic device with the massaging attachment positioned on a massaged surface 89 of a patient's body, in accordance with an exemplary scenario. The massaging attachment 75 allows therapeutic electrode 72 to be held at a certain distance D from the surface 89 of the massaged body. The distance D is adjusted by loosening thumb nuts 76,77 and moving massaging attachment 75 along guide slots 86,87. As the length of the gap D decreases, conditions arise for a spark discharge between the therapeutic electrode 72 and the massaged surface 89 of the patient's body. The sparks additionally induce pulse microcurrents in the patient's body. The wand 88 is held over a massaged surface 89 at an angle of about 30 degrees and moved along the surface 89. Cogwheels 81 or smooth pipe 82 provide a massage of the surface 89.

When the user presses the button 83 of the portable electrotherapy device, the DC motor 65 starts rotating clockwise and counterclockwise alternately, switching the direction of rotation at a predetermined frequency. A DC motor 65 drives pulley 66 through the driving pulleys 78 and 80 and a driving belt 79. Accordingly, the therapeutic electrode 72 alternately accumulates electric charge of one polarity, then another. An electrical charge of polarity opposite to that of the therapeutic electrode 72 is released through the therapeutic electrode 73 and the user's palm into the user's body. The massaging attachment 75 allows therapeutic electrode 72 to be held at a certain distance D from the surface 89 of a patient's body. As a result, an alternating electric field is formed between the therapeutic electrode 72 and the patient's body, which in turn induces microcurrents in the patient's body.

A user can change the frequency of the polarity switching using the push button 83 and the LED 84. A certain sequence of short and long presses allows the user to enter the programming mode. In this mode, the user can set the polarity reversal period by holding the button 83 pressed for a time equal to this period. The PCB 63 contains a microprocessor circuit for recognizing the pressing sequences of the button 83. The battery 62 is charged through the external power connector 64 and a battery charging controller on the PCB 63.

Figure 19:
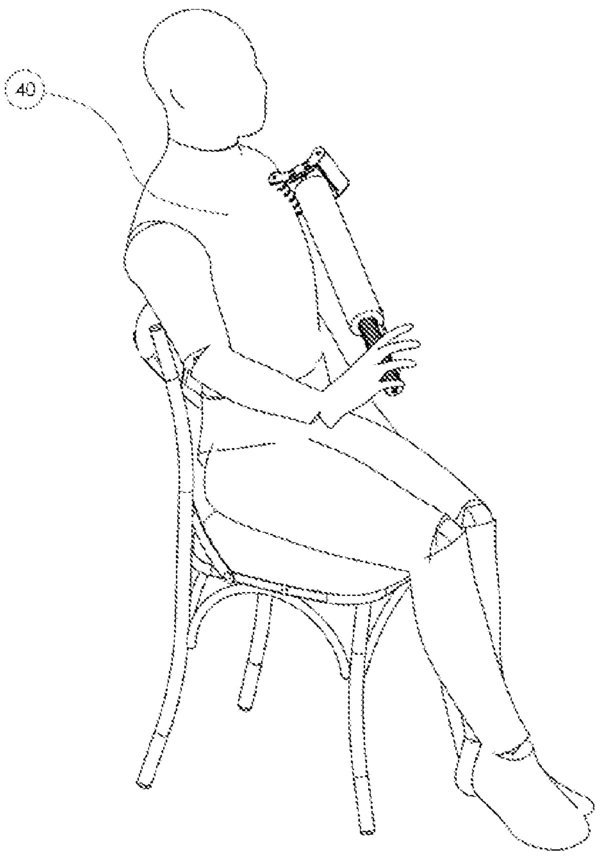
FIG. 19 illustrates an exemplary scenario of using the electrostatic therapeutic device of FIG. 14, 15 for self-treatment by a patient, in accordance with an exemplary scenario.

FIG. 19 illustrates an exemplary scenario of using the electrostatic therapeutic device of FIG. 13-18, for self-treatment by a patient 40, in accordance with an exemplary scenario. For example, consider the patient 40 sits on a chair and holds the wand so that the hollow therapeutic electrode creates an alternate electric field in the region of the user's left shoulder.

Figure 20:
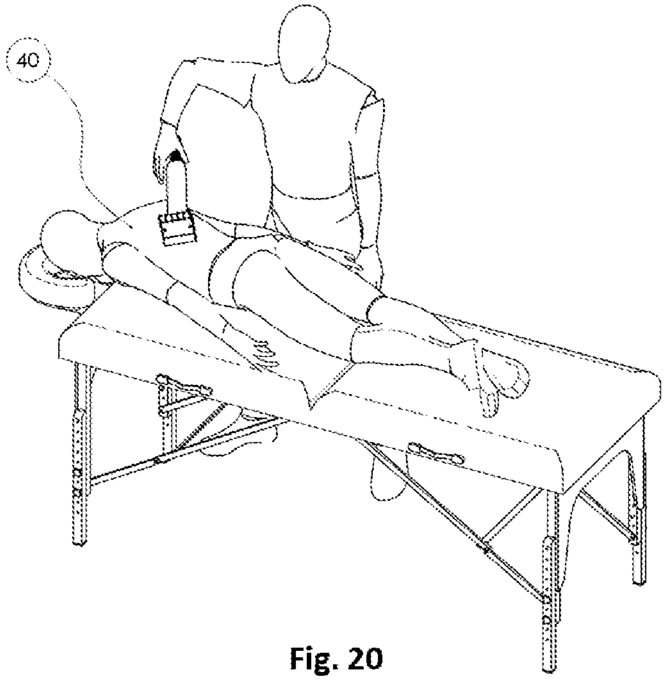
FIG. 20 illustrates an exemplary scenario of using the electrostatic therapeutic device of FIG. 14,15 by an operator on back of a patient, in accordance with an exemplary scenario.

FIG. 20 illustrates of an exemplary scenario of using the electrostatic therapeutic device of FIG. 14,15 by an operator on back of a patient 40, in accordance with an exemplary scenario. For example, consider an operator treats a patient lying on an isolated platform. The operator touches the body of the patient with one hand and holds the wand with the other hand, moving it over the body of the patient. Through the wand handle, electric charge of one polarity is supplied to the bodies of the operator and patient 40, and electric charge of the opposite polarity is supplied to the hollow therapeutic electrode in the wand. An alternate electric field is generated between the hollow therapeutic electrode in the wand and the body of the patient.

Figure 21:
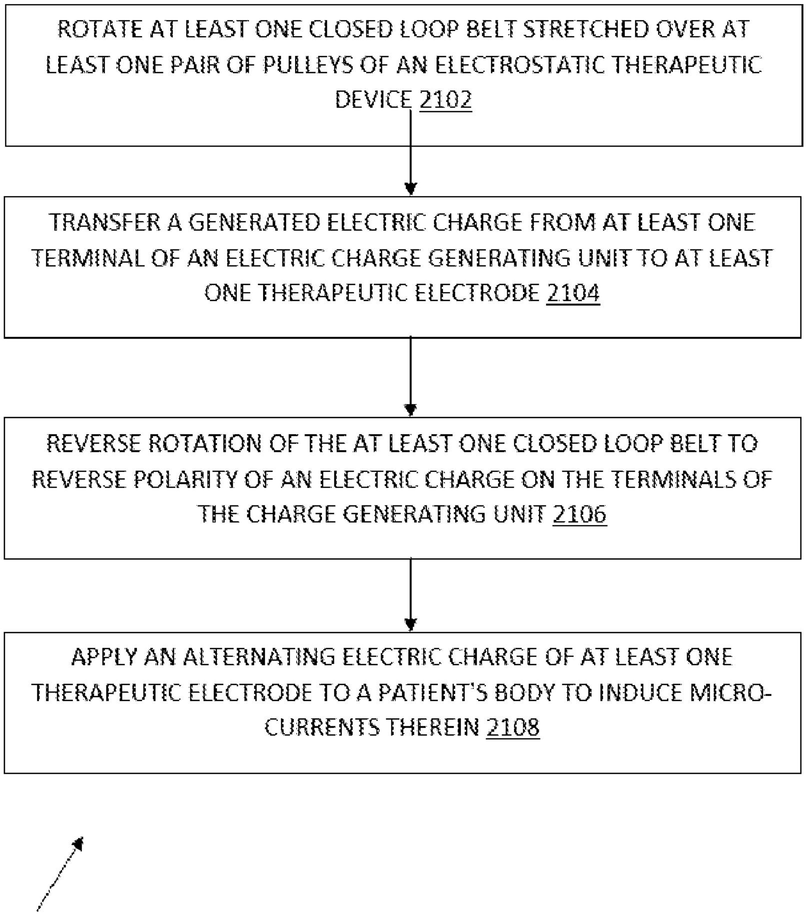
FIG. 21 depicts a flow diagram illustrating a method of therapeutic treatment, in accordance with an embodiment.

FIG. 21 depicts a flow diagram illustrating a method 2100 of therapeutic treatment, in accordance with an embodiment. In an embodiment, at step 2102, at least one closed loop belt stretched over at least one pair of pulleys of an electrostatic therapeutic device is rotated. Upon rotation of the at least one pair of pulleys, the at least one closed loop belt moves around the at least one pair of pulleys and an electric charge of a predetermined polarity is triboelectrically generated at a surface of the at least one closed loop belt and transferred with at least one closed loop belt between two terminals of an electric charge generating unit of an electrostatic therapeutic device. At step 2104, the generated electric charge is transferred from at least one terminal of an electric charge generating unit to at least one therapeutic electrode. At step 2106 rotation of the at least one closed loop belt is reversed to reverse polarity of an electric charge on the terminals of the charge generating unit. At step 2108 an alternating electric charge of at least one therapeutic electrode is applied to the body of a patient to induce micro-currents therein.

In an embodiment, a patient is placed on a dielectric platform and at least one therapeutic electrode is electrically connected to the body of the patient for transferring an electrical charge thereto.

In an embodiment, the patient is placed on a platform made of a dielectric material. The patient's body is placed in an electric field between at least two therapeutic electrodes of different polarities so that the patient's body is not in contact with them.

In an embodiment, the electrostatic therapeutic device is designed as a portable wand. A first therapeutic electrode is designed as a handle of the portable wand, and a patient or a therapist holds the handle of the portable wand to place a second therapeutic electrode over different areas of a body of the patient.

In an embodiment, at least one therapeutic electrode is positioned at a distance from the body of the patient.

In various embodiments, the electrostatic therapeutic device of the present technology solves all of the foregoing problems by providing a safe, lightweight, efficient, and easy to manufacture electrotherapy device for applying a high voltage alternating electric field to the body of a patient. The electrostatic therapeutic device of the present technology has no risk of malfunctions and failures caused by electrical breakdowns in the electrostatic therapeutic device, which can occur in a transformer or in high voltage semiconductor elements. Further, the electrostatic therapeutic device of the present technology does not have conductive points that could be dangerous to a user. Additionally, the electrostatic therapeutic device of the present technology does not require special circuits to protect a user from electric shock. Moreover, the electrostatic therapeutic device of the present technology acts on the patient with a high voltage electric field, inducing micro-currents in the patient's body as a whole or its specific target area.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

What is claimed is:

1. An electrostatic therapeutic device comprising:

i) a charge generating unit comprising:
   a. two parallel rotating shafts;
   b. at least one pair of pulleys mounted on the two parallel rotating shafts, wherein a first pulley from every pair of pulleys is mounted on a first shaft, and a second pulley from every pair of pulleys is mounted on a second shaft, wherein the pair of pulleys are made of a dielectric material, and configured to be triboelectrically charged with an electric charge of same polarity based on a triboelectric interaction with a closed loop belt upon rotation of the two parallel rotating shafts;
   c. at least one closed loop belt stretched over the at least one pair of pulleys to transfer an electric charge between a pair of terminals of a charge generating unit, wherein the closed loop belt is made of a dielectric material;
   d. a pair of terminals of a charge generating unit, for coupling the charge generating unit with at least one therapeutic electrode;
   e. a pair of charging electrodes for charging the at least one closed loop belt, wherein a first charging electrode from among the pair of charging electrodes is positioned over the at least one belt against the pulleys mounted on the first shaft and connected to the first terminal of the charge generating unit, and wherein a second charging electrode from among the pair of charging electrodes is positioned over the belt against the pulleys mounted on the second shafts and connected to the second terminal of the charge generating unit; and
   f. a pair of discharging electrodes for discharging the at least one closed loop belt, wherein a first discharging electrode of the pair of discharging electrodes is positioned over the belt at a distance from the first shaft and electrically connected to the first terminal of the charge generating unit, and where a second discharging electrode from the pair of discharging electrodes is positioned over the same side of the belt as the first discharging electrode at a distance from the second shaft and electrically connected to the second terminal of the charge generating unit, ii) the at least one therapeutic electrode coupled with the at least one terminal of the two terminals of the charge generating unit to enable applying an electrical charge to the patient's body, wherein every therapeutic electrode is coupled with only one of the two terminals of the charge generating unit;

iii) an electric drive unit to rotate the pair of shafts and the at least one closed loop belt in a clockwise direction and an anticlockwise direction; and iv) an electric circuit to switch the rotation of an electric drive with a predetermined frequency, whereby the electric charge generated due to the triboelectric interaction between the at least one closed loop belt and the at least one pair of dielectric pulleys is transferred to the at least one therapeutic electrode, wherein the at least one therapeutic electrode accumulates the electric charge of a predetermined polarity when the at least one pair of pulleys and the at least one closed loop belt rotate in the clockwise direction, and wherein the at least one therapeutic electrode accumulates the electric charge of a reverse polarity when the at least one pair of pulleys and the at least one closed loop belt rotate in the anti-clockwise direction, and wherein the body of the patient is therapeutically treated by micro-currents caused by an alternating electric charge on the at least one therapeutic electrode.

2. The electrostatic therapeutic device of claim 1, comprising a shell made of a conductive or a semi conductive material, and coupled with a terminal of the charge generating unit, wherein one charging electrode and one discharging electrode connected to the same terminal of the charge generating unit are located inside the shell to improve electric charge transfer between the at least one closed loop belt and the charging and discharging electrodes.

3. The electrostatic therapeutic device of claim 1, wherein one of the terminals of the charge generating unit is grounded.

4. The electrostatic therapeutic device of claim 2, wherein a first therapeutic electrode is shaped as a handle for holding the therapeutic device by a patient or therapist, and wherein when electric motor rotates, electric charge of one polarity is released into body of the patient or therapist via the handle, and electric charge of the opposite polarity is accumulated at a second therapeutic electrode placed at a distance over the body of a patient.

5. The electrostatic therapeutic device of claim 1, further comprising an attachment to hold the at least one therapeutic electrode at a predetermined distance from the body of a patient.

6. A method (2100) of therapeutic treatment comprising:

a. rotating (2102) at least one closed loop belt stretched over at least one pair of pulleys of an electrostatic therapeutic device, wherein upon rotation of the at least one pair of pulleys, the at least one closed loop belt moves around the at least one pair of pulleys and an electric charge of a predetermined polarity is triboelectrically generated at a surface of the at least one closed loop belt and transferred with at least one closed loop belt between two terminals of an electric charge generating unit of an electrostatic therapeutic device;

b. transferring (2104) the generated electric charge from at least one terminal of an electric charge generating unit to at least one therapeutic electrode;

c. reversing (2106) rotation of the at least one closed loop belt to reverse polarity of an electric charge on the terminals of the charge generating unit; and d. applying (2108) an alternating electric charge of at least one therapeutic electrode to the body of a patient to induce micro-currents therein.

7. The method of claim 6, wherein a patient is placed on a dielectric platform and wherein at least one therapeutic electrode is electrically connected to the body of the patient for transferring an electrical charge thereto.

8. The method of claim 6, wherein the patient is placed on a platform made of a dielectric material, wherein the patient's body is placed in an electric field between at least two therapeutic electrodes of different polarities so that the patient's body is not in contact with them.

9. The method of claim 6, wherein the electrostatic therapeutic device is designed as a portable wand, wherein a first therapeutic electrode is designed as a handle of the portable wand, and wherein a patient or a therapist holds the handle of the portable wand to place a second therapeutic electrode over different areas of a body of the patient.

10. The method of claim 7, wherein at least one therapeutic electrode is positioned at a distance from the body of the patient.

* * * * *